US006440680B1

(12) United States Patent
Ford-Hutchinson et al.

(10) Patent No.: US 6,440,680 B1
(45) Date of Patent: Aug. 27, 2002

(54) METHODS OF IDENTIFYING MODULATORS OF PROSTAGLANDIN RECEPTOR EP1

(75) Inventors: Anthony Ford-Hutchinson, Beaconsfield (CA); Colin Funk, Nashville, TN (US); Richard Grygorczyk, Dollard des Ormeaux; Kathleen Metters, Montreal, both of (CA)

(73) Assignees: Merck Frosst Canada, Inc., Kirkland (CA); Vanderbuilt University, Nashville, TN (US)

( * ) Notice: Subject to any disclaimer, the term of this patent is extended or adjusted under 35 U.S.C. 154(b) by 0 days.

(21) Appl. No.: 09/395,366

(22) Filed: Sep. 13, 1999

Related U.S. Application Data

(62) Division of application No. 09/255,671, filed on Feb. 23, 1999, now Pat. No. 6,031,079, which is a division of application No. 08/068,729, filed on May 26, 1993, now Pat. No. 5,985,597.

(51) Int. Cl.$^7$ .................. G01N 33/53; C12N 15/00; C12N 5/00
(52) U.S. Cl. .................. 435/7.1; 435/7.2; 435/70.1; 435/320.1; 435/325; 436/501
(58) Field of Search .................. 435/7.1, 7.2, 70.1, 435/325, 320.1; 530/350; 436/501

(56) References Cited

U.S. PATENT DOCUMENTS 5,985,597 A * 11/1999 Ford-Hutchnson et al. 435/69.1
6,031,079 A * 2/2000 Ford-Hutchinson et al. ..... 530/350

OTHER PUBLICATIONS

Current Protocols in Molecular Biology, (vol. 3) pp. 10.0.1–10.0.19,17.8.1–17.8.6 Copyright 1998 John Wiley & Sons, Inc.*
R. Coleman, et al., Characterization Of The Prostanoid Receptors Mediating Contraction of Guinea–Pig Isolated Trachea, (1985), Prostaglandins, 29, pp. 363–375.
P. Davies, et. al., Prostaglandins and Inflammation, (1992), Inflammation: Basic Principles And Clinical Correlates, Gallin, Goldstein, Snyderman, eds., 2nd Ed., pp. 123–138.
E. Horton, et al., Uterine Luteolytic Hormone: A Physiological Role for Prostaglandin F2a, (1976), Physiol. Rev., 56, pp. 595–651.
D. DeWitt, Prostaglandin endoperoxide synthase: regulation of enzyme expression, (1991), Biochim. Biophys, Acta, 1083, pp. 121–134.
J. Stjernschantz,et al., Phenyl substituted prostaglandin analogs for glaucoma treatment, (1992), Drugs Future, 17, pp. 691–704.

P. Racz, et al., Maintained Intraocular Pressure Reduction With Once–a–Day Application of a New Prostaglandin F2a Analogue (PhXA41), (1993), Arch. Opthalmol., 111, pp. 657–661.
J. Senior, et al., In vitro characterization of prostanoid FP–, DP–, IP– and TP–receptors on the non–pregnant human myometrium, (1992), Brit. J. Pharmacol., 107, pp. 215–221.
J. Senior, et al., In vitro characterization of prostanoid receptors on human myometrium at term pregnancy, (1993), Brit. J. Pharmacol., 108, pp. 501–506.
J. Csepli, et al., The Effect Of The Prostaglandin F2a Analogue ICI 81008 On Uterine Small Arteries And On Blood Pressure, (1975), Prostaglandins, 10, pp. 689–697.
R. Coleman, Methods in prostanoid receptor classification, (1987), Prostaglandins And Related Substances—A Practical Approach, IRL Press, 1st Ed., pp. 267–303.
R. Coleman, et al., A study of the prostanoid receptors mediating bronchocorstriction in the anaesthetized guinea–pig and dog, (1981), Brit. J. Pharmacol., 74, p. 913.
J. Barnard, et al., Evaluation of prostaglandin F2a and prostacyclin interactions in the isolated perfused rat lung, (1992), J. Appl. Physiol., 72, pp. 2469–2474.
J. Davis, et al., Prostaglandin F2a stimulates phosphatidylinositol 4,5–biphosphate hydrolysis and mobilizes intracellular Ca2+ in bovine luteal cells, (1987), Proc. Natl. Acad. Sci. U.S.A. 84, pp. 3728–3732.
J. Kitanaka, et al., Astrocytes Possess Prostaglandin F2a Receptors Coupled To Phospholipase C, (1991), Biochem. Biophys. Res. Comm., 178, pp. 946–952.
F. Black, et al., Activation of inositol phospholipid breakdown by prostaglandin F2a without any stimulation of proliferation in quiescent NIH–3T3 fibroblasts, (1990), Biochem. Journal, 266, pp. 661–667.
A. Nakao, et al., Characterization of Prostaglandin F2a Receptor of Mouse 3T3 Fibroblasts and Its Functional Expression in Xenopus Laevis Oocytes, (1993), J. Cell Physiol., 155, pp. 257–264.
W. Powell, et al., Prostaglandin F2a Receptor in Ovine corpora lutea, (1974), Eur. J. Biochem., 41, pp. 103–107.
W. Powell, et al., Occurrence and Properties of a Prostaglandin F2a Receptor in Bovine Corpora Lutea, (1975), Eur. J. Biochem., 56, pp. 73–77.
W. Powell, et al., Localization of a Prostaglandin F2a Receptor in Bovine Corpus luteum Plasma Membranes, (1976), Eur. J. Biochem., 61, pp. 605–611.

(List continued on next page.)

Primary Examiner—Elizabeth Kemmerer
Assistant Examiner—Regina M. DeBerry
(74) Attorney, Agent, or Firm—J. Mark Hand; Jack L. Tribble

(57) ABSTRACT

A novel prostaglandin receptor has been identified and DNA encoding the receptor has been isolated, purified, sequenced and expressed in host cells. This DNA encoding the novel prostaglandin receptor and host cells expressing the receptor are used to identify modulators of the prostaglandin receptor.

26 Claims, 7 Drawing Sheets

OTHER PUBLICATIONS

M. Molnar, et al., PGF2a and PGE2 binding to rat myometrium during gestation, paturition, and postpartum, (1990), Am. J. Physiol., 258, pp. E740–E747.

Th. Bauknecht, et al., Distribution of prostaglandin E2 and prostaglandin F2a receptors in human myometrium, (1981), Acta Endocrinol., 98, pp. 446–450.

F. Neuschafer–Rube, et al., Characterization of prostaglandin–F2a–binding sites on rat hepatocyte plasma membranes, (1993), Eur. J. Biochem., 211, pp. 163–169.

M. Hirata, et al., Cloning and expression of cDNA for a human thromboxane A2 receptor, (1991), Nature, 349, pp. 617–620.

A. Honda, et al., Cloning and Expression of a cDNA for Mouse Prostaglandin E Receptor EP2 Subtype*, (1993), J. Biol. Chem., 268, pp. 7759–7762.

Y. Sugimoto, et al., Two Isoforms of the EP3 Receptor with Different Carboxyl–terminal Domains, (1993), J. Biol. Chem., 268, pp. 2712–2718.

Y. Sugimoto, et al., Cloning and Expression of a cDNA for Mouse Prostaglandin E Receptor EP3 Subtype*, (1992), J. Biol. Chem., 267, pp. 6463–6466.

K. Bunce, et al., Differential Effects Of Prostaglandins On Unidirectional Absorption And Secretion In Rat Ileum, (1987), Gastroenterology, 92, p. 1332.

Y. Dong, et al., Prostaglandin E receptor subtypes in smooth muscle: agonist activities of stable prostacyclin analogues, (1986), Br. J. Pharmacol., 87, pp. 97–107.

B. Hedqvist, et al., Prostaglandin–Induced Neurotransmission Failure In The Field–Stimulated, Isolated Vas Deferens, (1972), Neuropharmacology, 11, pp. 177–187.

M. McKenniff, et. al., Characterisation of receptors mediating the contractile effects of prostanoids in guinea–pig and human airways, (1988), Eur. J. Pharmacol., 153, pp. 149–159.

R. Eglen, et al., The action of prostanoid receptor agonists and antagonists on smooth muscle and platelets, (1988), Br. J. Pharmacol., 94, pp. 591–601.

J. Louttit, et al., Prostanoid EP–Receptors In Pig Saphenous Vein, (7/26–31/92) , 8th International Conf. on Prostaglandins, Abstract 258.

R. Lawrence, et al., Investigation of the prostaglandin E (EP–) receptor subtype mediating relaxation of the rabbit jugular vein, (1992), Br. J. Pharmacol., 105, pp. 817–824.

R. Coleman, et al., Prostanoids and their Receptors, (1989), Comprehensive Medicinal Chemistry, 3, pp. 643–714.

W. Campbell, et al., Lipid–Derived Autacoids: Eicosanoids And Platelet–Activating Factor, (1990), The Pharmacological Basis of Therapeutics, 8th Edition, pp. 600–617.

Masu et al., "cDNA cloning of bovine substance K receptor . . . expression system", Nature, vol. 329, p 386 (1987).

Funk et al. "Cloning and expression of a cDNA. . . Receptor EP1 subtype", J. Biol. Chem. vol. 268, pp. 26767–26772 (1993).

* cited by examiner

GGGGGCGGCAGGGCTGAGCGGCCGGTGATGGGGACCCCACATCCCAGGCAGTGCCGGCACCCCTGGCGCCTGAC

ATG AGC CCT TGC GGG CCC CTC AAC CTG AGC CTG GCG GGC GAG GCG ACC ACA TGC GCG GCG CCC TGG GTC CCC AAC

ACG TCG GCC GTG CCG CCG TCG GGC GCT TCG CCC GCG CTG CCC ATC TTC TCC ATG ACG CTG GGC GCC GTG TCC AAC

CTG CTG GCG CTG GCG CTG CTG GCG CAG GCC GCG GGC CGC CTG CGA CGC CGC CGC TCG GCC ACC ACC TTC CTG CTG

TTC GTG GCC AGC CTG CTG GCC ACC GAC CTG GCG GGC CAC GTG ATC CCG GGC GCG CTG GTG CTG CGT CTG TAC ACT

GCG GGG CGC GCT CCG GCC GGC GGG GCC TGC CAC TTC CTG GGC GGC TGC ATG GTC TTC TTC GGC CTG TGC CCG CTG

CTG CTG GGC TGT GGC ATG GCC GTG GAG CGC TGC GTG GGC GTC ACG CGG CCG CTG CTC CAC GCC GCG CGG GTC TCG

GTC GCC CGC GCG CGC CTG GCG CTG GCC GCG GTG GCC GCG GTG GCC TTG GCC GTG GCG CTG CTG CCG CTG GCG CGC

GTG GGC CGC TAT GAG CTG CAG TAC CCG GGC ACG TGG TGC TTC ATC GGC CTG GGT CCC CCG GGC GGC TGG CGC CAG

GCA CTG CTT GCT GGC CTC TTC GCC AGC CTC GGC CTG GTC GCG CTC CTC GCC GCG CTG GTG TGC AAC ACG CTC AGC

GGC CTG GCC CTG CAT CGC GCC CGC TGG CGA CGC CGC TCC CGA CGG CCT CCC CCG GCC TCA GGC CCC GAC AGC CGG

CGT CGC TGG GGG GCG CAC GGA CCC CGC TCG GCC TCC GCC TCG TCC GCC TCG TCC ATC GCT TCG GCC TCC ACC TTC

TTT GGC GGC TCT CGG AGC AGC GGC TCG GCA CGC AGA GCT CGC GCC CAC GAC GTG GAG ATG GTG GGC CAG CTT GTC

GGT ATC ATG GTG GTG TCG TGC ATC TGC TGG AGC CCA ATG CTG GTG TTG GTG GCG CTG GCC GTC GGC GGC TGG AGC

TCT ACC TCC CTG CAG CGG CCA CTG TTC CTG GCC GTG CGC CTT GCC TCC TGG AAC CAG ATC CTG GAC CCT TGG GTG

TAC ATC CTA CTG CGC CAG GCC GTG CTG CGC CAA CTG CTT CGC CTC TTG CCC CCG AGG GCC GGA GCC AAG GGC GGC

CCC GCG GGG CTG GGC CTA ACA CCG AGC GCC TGG GAG GCC AGC TCG CTG CGC AGC TCC CGG CAC AGC GGC CTC AGC

CAC TTC TAA GCACAACCAGAGGCCCAACGACTAAGCCAGCCCACCCTGGGCTGGGCCCAGCTGCGCGGCGCAGAGCCTTTGGGAATAAAAAGCCAT

TCTGCGAAAAAAAAAAAAAAAAAAA (SEQ ID NO: 3)

FIG.1

MET Ser Pro Cys Gly Pro Leu Asn Leu Ser Leu Ala Gly Glu Ala Thr Thr Cys Ala Ala Pro Trp Val Pro Asn    25

Thr Ser Ala Val Pro Pro Ser Gly Ala Ser Pro Ala Leu Pro Ile Phe Ser MET Thr Leu Gly Ala Val Ser Asn    50

Leu Leu Ala Leu Ala Leu Leu Ala Gln Ala Ala Gly Arg Leu Arg Arg Arg Ser Ala Thr Thr Phe Leu Leu    75

Phe Val Ala Ser Leu Leu Ala Thr Asp Leu Ala Gly His Val Ile Pro Gly Ala Leu Val Leu Arg Leu Tyr Thr    100

Ala Gly Arg Ala Pro Ala Gly Gly Ala Cys His Phe Leu Gly Gly Cys MET Val Phe Gly Leu Cys Pro Leu    125

Leu Leu Gly Cys Gly MET Ala Val Glu Arg Cys Val Gly Val Thr Arg Pro Leu Leu His Ala Ala Arg Val Ser    150

Val Ala Arg Ala Arg Leu Ala Leu Ala Ala Val Ala Ala Val Ala Leu Ala Val Ala Leu Leu Pro Leu Ala Arg    175

Val Gly Arg Tyr Glu Leu Gln Tyr Pro Gly Thr Trp Cys Phe Ile Gly Leu Gly Pro Pro Gly Gly Trp Arg Gln    200

Ala Leu Leu Ala Gly Leu Phe Ala Ser Leu Gly Leu Val Ala Leu Leu Ala Ala Leu Val Cys Asn Thr Leu Ser    225

Gly Leu Ala Leu His Arg Ala Arg Trp Arg Arg Arg Ser Arg Arg Pro Pro Pro Ala Ser Gly Pro Asp Ser Arg    250

Arg Arg Trp Gly Ala His Gly Pro Arg Ser Ala Ser Ala Ser Ser Ala Ser Ser Ile Ala Ser Ala Ser Thr Phe    275

Phe Gly Gly Ser Arg Ser Ser Gly Ser Ala Arg Arg Ala Arg Ala His Asp Val Glu MET Val Gly Gln Leu Val    300

Gly Ile MET Val Val Ser Cys Ile Cys Trp Ser Pro MET Leu Val Leu Val Ala Leu Ala Val Gly Gly Trp Ser    325

Ser Thr Ser Leu Gln Arg Pro Leu Phe Leu Ala Val Arg Leu Ala Ser Trp Asn Gln Ile Leu Asp Pro Trp Val    350

Tyr Ile Leu Leu Arg Gln Ala Val Leu Arg Gln Leu Leu Arg Leu Leu Pro Pro Arg Ala Gly Ala Lys Gly Gly    375

Pro Ala Gly Leu Gly Leu Thr Pro Ser Ala Trp Glu Ala Ser Ser Leu Arg Ser Ser Arg His Ser Gly Leu Ser    400

His Phe   (SEQ ID NO: 4)                                                                                402

FIG.2

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

CTGTCCTTCC TGCTGAACAC GGTCAGCGTG        30

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
GCGGCGGAAC AGGATATACA CC                                              22
```

(2) INFORMATION FOR SEQ ID NO:3:

(i) SEQUENCE CHARACTERISTICS:
        (A) LENGTH: 1394 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGGGGCGGCA GGGCTGAGCG GCCGGTGATG GGGACCCCAC ATCCCAGGCA GTGCCGGCAC      60
CCCTGGCGCC TGACATGAGC CCTTGCGGGC CCCTCAACCT GAGCCTGGCG GGCGAGGCGA     120
CCACATGCGC GGCGCCCTGG GTCCCCAACA CGTCGGCCGT GCCGCCGTCG GGCGCTTCGC     180
CCGCGCTGCC CATCTTCTCC ATGACGCTGG GCGCCGTGTC CAACCTGCTG GCGCTGGCGC     240
TGCTGGCGCA GGCCGCGGGC CGCCTGCGAC GCCGCCGCTC GGCCACCACC TTCCTGCTGT     300
TCGTGGCCAG CCTGCTGGCC ACCGACCTGG CGGGCCACGT GATCCCGGGC GCGCTGGTGC     360
TGCGTCTGTA CACTGCGGGG CGCGCTCCGG CCGGCGGGGC CTGCCACTTC CTGGGCGGCT     420
GCATGGTCTT CTTCGGCCTG TGCCCGCTGC TGCTGGGCTG TGGCATGGCC GTGGAGCGCT     480
GCGTGGGCGT CACGCGGCCG CTGCTCCACG CCGCGCGGGT CTCGGTCGCC CGCGCGCGCC     540
TGGCGCTGGC CGCGGTGGCC GCGGTGGCCT TGGCCGTGGC GCTGCTGCCG CTGGCGCGCG     600
TGGGCCGCTA TGAGCTGCAG TACCCGGGCA CGTGGTGCTT CATCGGCCTG GGTCCCCCGG     660
GCGGCTGGCG CCAGGCACTG CTTGCTGGCC TCTTCGCCAG CCTCGGCCTG GTCGCGCTCC     720
TCGCCGCGCT GGTGTGCAAC ACGCTCAGCG GCCTGGCCCT GCATCGCGCC CGCTGGCGAC     780
GCCGCTCCCG ACGGCCTCCC CCGGCCTCAG GCCCCGACAG CCGGCGTCGC TGGGGGGCGC     840
ACGGACCCCG CTCGGCCTCC GCCTCGTCCG CCTCGTCCAT CGCTTCGGCC TCCACCTTCT     900
TTGGCGGCTC TCGGAGCAGC GGCTCGGCAC GCAGAGCTCG CGCCCACGAC GTGGAGATGG     960
TGGGCCAGCT TGTCGGTATC ATGGTGGTGT CGTGCATCTG CTGGAGCCCA ATGCTGGTGT    1020
TGGTGGCGCT GGCCGTCGGC GGCTGGAGCT CTACCTCCCT GCAGCGGCCA CTGTTCCTGG    1080
CCGTGCGCCT TGCCTCCTGG AACCAGATCC TGGACCCTTG GGTGTACATC CTACTGCGCC    1140
AGGCCGTGCT GCGCCAACTG CTTCGCCTCT TGCCCCCGAG GGCCGGAGCC AAGGGCGGCC    1200
CCGCGGGGCT GGGCCTAACA CCGAGCGCCT GGGAGGCCAG CTCGCTGCGC AGCTCCCGGC    1260
ACAGCGGCCT CAGCCACTTC TAAGCACAAC CAGAGGCCCA ACGACTAAGC CAGCCCACCC    1320
TGGGCTGGGC CCAGGTGCGC GGCGCAGAGC TTTGGGAATA AAAAGCCATT CTGCGAAAAA    1380
AAAAAAAAAA AAAA                                                    1394
```

(2) INFORMATION FOR SEQ ID NO:4:

(i) SEQUENCE CHARACTERISTICS:
    (A) LENGTH: 402 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:4:

```
Met Ser Pro Cys Gly Pro Leu Asn Leu Ser Leu Ala Gly Glu Ala Thr
1               5                   10                  15

Thr Cys Ala Ala Pro Trp Val Pro Asn Thr Ser Ala Val Pro Pro Ser
                20                  25                  30

Gly Ala Ser Pro Ala Leu Pro Ile Phe Ser Met Thr Leu Gly Ala Val
            35                  40                  45

Ser Asn Leu Leu Ala Leu Ala Leu Leu Ala Gln Ala Ala Gly Arg Leu
50                  55                  60

Arg Arg Arg Arg Ser Ala Thr Thr Phe Leu Leu Phe Val Ala Ser Leu
65                  70                  75                  80

Leu Ala Thr Asp Leu Ala Gly His Val Ile Pro Gly Ala Leu Val Leu
                85                  90                  95

Arg Leu Tyr Thr Ala Gly Arg Ala Pro Ala Gly Gly Ala Cys His Phe
                100                 105                 110

Leu Gly Gly Cys Met Val Phe Phe Gly Leu Cys Pro Leu Leu Leu Gly
                115                 120                 125

Cys Gly Met Ala Val Glu Arg Cys Val Gly Val Thr Arg Pro Leu Leu
                130                 135                 140

His Ala Ala Arg Val Ser Val Ala Arg Ala Arg Leu Ala Leu Ala Ala
145                 150                 155                 160

Val Ala Ala Val Ala Leu Ala Val Ala Leu Leu Pro Leu Ala Arg Val
                165                 170                 175

Gly Arg Tyr Glu Leu Gln Tyr Pro Gly Thr Trp Cys Phe Ile Gly Leu
                180                 185                 190

Gly Pro Pro Gly Gly Trp Arg Gln Ala Leu Leu Ala Gly Leu Phe Ala
                195                 200                 205

Ser Leu Gly Leu Val Ala Leu Leu Ala Ala Leu Val Cys Asn Thr Leu
210                 215                 220

Ser Gly Leu Ala Leu His Arg Ala Arg Trp Arg Arg Ser Arg Arg
225                 230                 235                 240

Pro Pro Pro Ala Ser Gly Pro Asp Ser Arg Arg Trp Gly Ala His
                245                 250                 255

Gly Pro Arg Ser Ala Ser Ala Ser Ser Ala Ser Ile Ala Ser Ala
                260                 265                 270

Ser Thr Phe Phe Gly Gly Ser Arg Ser Ser Gly Ser Ala Arg Arg Ala
                275                 280                 285

Arg Ala His Asp Val Glu Met Val Gly Gln Leu Val Gly Ile Met Val
290                 295                 300

Val Ser Cys Ile Cys Trp Ser Pro Met Leu Leu Val Ala Leu Ala
305                 310                 315                 320

Val Gly Gly Trp Ser Ser Thr Ser Leu Gln Arg Pro Leu Phe Leu Ala
                325                 330                 335

Val Arg Leu Ala Ser Trp Asn Gln Ile Leu Asp Pro Trp Val Tyr Ile
                340                 345                 350

Leu Leu Arg Gln Ala Val Leu Arg Gln Leu Leu Arg Leu Leu Pro Pro
                355                 360                 365
```

```
Arg Ala Gly Ala Lys Gly Gly Pro Ala Gly Leu Gly Leu Thr Pro Ser
    370                 375                 380

Ala Trp Glu Ala Ser Ser Leu Arg Ser Ser Arg His Ser Gly Leu Ser
385                 390                 395                 400

His Phe (2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CTAGCGGATC CCGCCATGAG CCCTTGCGGG CC                                        32

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCAAGGGCT CATGGCGGAT CCG                                                  23
```

METHODS OF IDENTIFYING MODULATORS OF PROSTAGLANDIN RECEPTOR EP1

This application is a division of application Ser. No. 09/255,671, filed Feb. 23, 1999, now U.S. Pat. No. 6,031,079, which is a division of application Ser. No. 08/068,729, filed May 26, 1993, now U.S. Pat. No. 5,985,597.

This invention was made with government support under grant numbers HL 30400 and HL 02710 from the National Heart, Lung and Blood Institute (NHLBI). The United States Government has certain rights in this invention.

BACKGROUND OF THE INVENTION

The physiological actions of prostaglandin (PG)$E_2$ are mediated through interaction with the prostaglandin E receptor(s). There are three subtypes of the EP receptor, $EP_1$, $EP_2$ and $EP_3$ (for review see Coleman et al., 1989). These three subtypes all show high affinity for PGE2 but show differences in their affinities for various agonists and antagonists and exert their actions through different secondary transduction mechanisms. Thus activation of the EP1 receptor is associated with a rise in IP3 and intracellular calcium, activation of the EP2 receptor results in a rise in intracellular cyclic AMP and activation of the EP3 receptor a fall in intracellular cyclic AMP followed by a rise in intracellular calcium. To date the only members of this family to be cloned are the mouse $EP_2$ (Honda et al., 1993) and the mouse $EP_{3\alpha}$ and $EP_{3\beta}$ (Sugimoto et al., 1992; Sugimoto et al., 1993) subtypes. EP1 receptors are normally found on a wide variety of cells including the small intestine, kidney, stomach, muscle, eye, uterus and trachea, in humans and other animals. Binding of prostaglandin to the EP1 receptor protein elicits an increase in intracellular calcium levels. This signal causes the tissues to respond, for example, by muscle contraction.

SUMMARY OF THE INVENTION

A novel prostaglandin receptor protein termed EP1 has been identified from human cells. A DNA molecule encoding the full length EP1 protein has been isolated and purified, and the nucleotide sequence has been determined. The EP1 encoding DNA has been cloned into expression vectors and these expression vectors, when introduced into recombinant host cells, cause the recombinant host cells to express a functional EP1 receptor protein. The novel EP1 protein, the EP1-encoding DNA, the expression vectors and recombinant host cells expressing recombinant EP1 are useful in the identification of modulators of EP1 receptor activity.

A method of identifying EP1 receptor modulators is also disclosed which utilizes the recombinant EP1 expressing host cells. Modulators of EP1 activity are useful for the treatment of prostaglandin-related diseases and for modulating the effects of prostaglandin on the EP1 receptor.

BRIEF DESCRIPTION OF THE DRAWINGS

FIG. 1—The complete DNA sequence encoding the EP1 receptor protein is shown.

FIG. 2—The complete deduced amino acid sequence of the EP1 receptor protein is shown.

DETAILED DESCRIPTION OF THE INVENTION

Figure 3A:
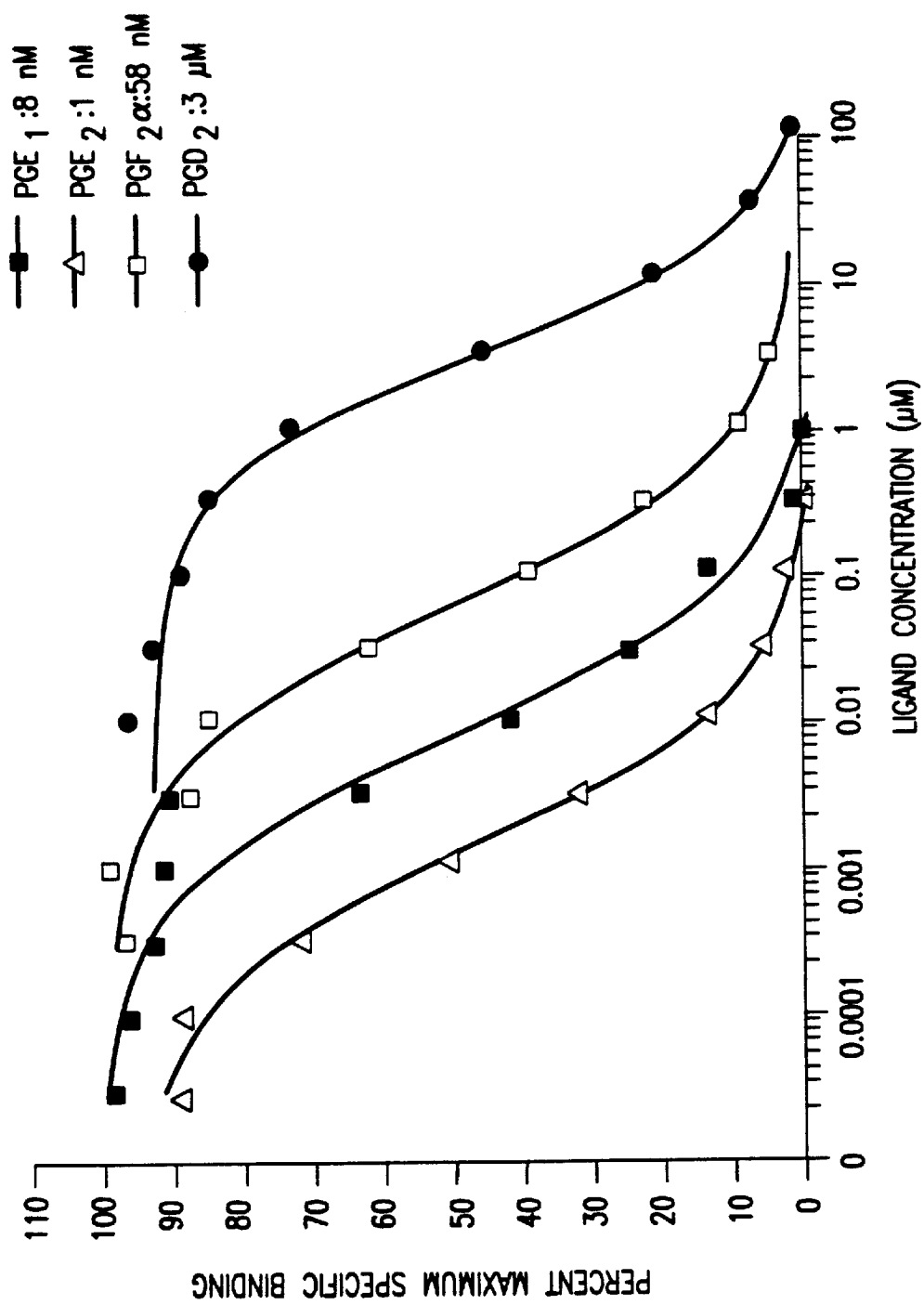
FIGS. 3A–3B—Competition for [$^3$H]$PGE_2$ binding to pcDNA-EP1-transfected COS-M6 membranes: [$^3$H]$PGE_2$ binding assays were performed as described in the Methods in the presence of Panel A: 0.03 nM–10 $\mu$M $PGE_2$ (Δ), $PGE_1$ (■), $PGF_{2\alpha}$ (□), $PGD_2$ (●), Panel B: 3 nM–100 $\mu$M AH6809 (○), SC19220 (▲), and Butaprost (◊). Butaprost and AH 6809 were generous gifts from Miles Inc. and Glaxo Group Research Ltd.

The present invention relates to cDNA encoding a novel prostaglandin receptor termed EP1. The present invention is also related to recombinant host cells which express the cloned EP1-encoding DNA contained in a recombinant expression plasmid. The present invention is also related to a method for the screening of substances which modulate EP1 receptor activity. The DNA of the present invention is isolated from EP1 producing cells. EP1, as used herein, refers to a G protein-coupled receptor which can specifically bind prostaglandin molecules. The present invention also relates to a unique prostaglandin receptor protein, also described as EP1, which is isolated from EP1 producing cells. EP1 receptor protein, as used herein, refers to a G protein-coupled type receptor which can specifically bind prostaglandin molecules.

Mammalian cells capable of producing EP1 include, but are not limited to, cells derived from small intestine, kidney, stomach, muscle, eye, uterus and trachea. Transformed mammalian cell lines which produce EP1 include, but are not limited to, HEL cells. The preferred cells for the present invention include normal human kidney cells and the most preferred cells are human erythroleukemia cells.

Other cells and cell lines may also be suitable for use to isolate EP1 cDNA. Selection of suitable cells may be done by screening for EP1 on cell surfaces. Methods for detecting EP1 activity are well known in the art and measure the binding of radiolabelled ligand specific for the receptor. Cells which possess EP1 activity in this assay may be suitable for the isolation of EP1 cDNA.

Any of a variety of procedures may be used to clone EP1 cDNA. These methods include, but are not limited to, direct functional expression of the EP1 cDNA following the construction of an EP1-containing cDNA library in an appropriate expression vector system. Another method is to screen an EP1-containing cDNA library constructed in a bacteriophage or plasmid shuttle vector with a labelled oligonucleotide probe designed from the amino acid sequence of the EP1 protein. The preferred method consists of screening an EP1-containing cDNA library constructed in a bacteriophage or plasmid shuttle vector with a partial cDNA encoding the EP1 protein. This partial cDNA is obtained by the specific PCR amplification of EP1 DNA fragments through the design of degenerate oligonucleotide primers from the amino acid sequence known for other G protein-coupled receptors which are related to the prostaglandin EP1 receptors.

It is readily apparent to those skilled in the art that other types of libraries, as well as libraries constructed from other cells or cell types, may be useful for isolating EP1-encoding DNA. Other types of libraries include, but are not limited to, cDNA libraries derived from other cells or cell lines other than human erythroleukemia cells, and genomic DNA libraries.

It is readily apparent to those skilled in the art that suitable cDNA libraries may be prepared from cells or cell lines which have EP1 activity. The selection of cells or cell lines for use in preparing a cDNA library to isolate EP1 cDNA may be done by first measuring cell associated EP1 activity using the known labelled ligand binding assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding EP1 may also be isolated from a suitable genomic DNA library.

Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone the EP1 gene by one of the preferred methods, the amino acid sequence or DNA sequence of EP1 or a homologous protein is necessary. To accomplish this, EP1 protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial EP1 DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the EP1 sequence but others in the set will be capable of hybridizing to EP1 DNA even in the presence of DNA oligonucleotides with mismatches. The mismatched DNA oligonucleotides may still sufficiently hybridize to the EP1 DNA to permit identification and isolation of EP1 encoding DNA.

Using one of the preferred methods, cDNA clones encoding EP1 are isolated in a two-stage approach employing polymerase chain reaction (PCR) based technology and cDNA library screening. In the first stage, $NH_2$-terminal and internal amino acid sequence information from the purified EP1 or a homologous protein is used to design degenerate oligonucleotide primers for the amplification of EP1-specific DNA fragments. In the second stage, these fragments are cloned to serve as probes for the isolation of full length cDNA from a cDNA library derived from human erythroleukemia cells.

The sequence for the near full-length cDNA encoding EP1 is shown in Table 1, and was designated clone EP1. The deduced amino acid sequence of EP1 from the cloned cDNA is shown in Table 2. Inspection of the determined cDNA sequence reveals the presence of a single, large open reading frame that encodes for a 402 amino acid protein.

The cloned EP1 cDNA obtained through the methods described above may be recombinantly expressed by molecular cloning into an expression vector containing a suitable promoter and other appropriate transcription regulatory elements, and transferred into prokaryotic or eukaryotic host cells to produce recombinant EP1. Techniques for such manipulations can be found described in Maniatis, T. et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant EP1 in mammalian cells. Commercially available mammalian expression vectors which may be suitable for recombinant EP1 expression, include but are not limited to, pMC1neo (Stratagene), pXT1 (Stratagene), pSG5 (Stratagene), pcDNAI, pcDNAIamp (Invitrogen), EBO-pSV2-neo (ATCC 37593) pBPV-1(8-2) (ATCC 37110), pdBPV-MMTneo(342-12) (ATCC 37224), pRS-Vgpt (ATCC 37199), pRSVneo (ATCC 37198), pSV2-dhfr (ATCC 37146), pUCTag (ATCC 37460), and 1ZD35 (ATCC 37565).

DNA encoding EP1 may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce EP1 protein. Identification of EP1 expressing cells may be done by several means, including but not limited to immunological reactivity with anti-EP1 antibodies, and the presence of host cell-associated EP1 activity.

Expression of EP1 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the EP1 cDNA sequence(s) that yields optimal levels of receptor activity and/or EP1 protein, EP1 cDNA molecules including but not limited to the following can be constructed: the full-length open reading frame of the EP1 cDNA and various constructs containing portions of the cDNA encoding only specific domains of the receptor protein or rearranged domains of the protein. All constructs can be designed to contain none, all or portions of the 5' and/or 3' untranslated region of EP1 cDNA. $EP_1$ activity and levels of protein expression can be determined following the introduction, both singly and in combination, of these constructs into appropriate host cells. Following determination of the EP1 cDNA cassette yielding optimal expression in transient assays, this EP1 cDNA construct is transferred to a variety of expression vectors (including recombinant viruses), including but not limited to those for mammalian cells, plant cells, insect cells, oocytes, *E. Coli*, and yeast cells.

Mammalian cell transfectants are assayed for both the levels of EP1 receptor activity and levels of EP1 protein by the following methods. Assessing EP1 receptor activity involves the direct introduction of a labelled ligand to the cells and determining the amount of specific binding of the ligand to the EP1-expressing cells. Binding assays for receptor activity are known in the art (Frey et al., 1993, Eur. J. Pharmacol., 244, pp 239–250).

Levels of EP1 protein in host cells is quantitated by a variety of techniques including, but not limited to, immunoaffinity and/or ligand affinity techniques. EP1-specific affinity beads or EP1-specific antibodies are used to isolate $^{35}S$-methionine labelled or unlabelled EP1 protein. Labelled EP1 protein is analyzed by SDS-PAGE. Unlabelled EP1 protein is detected by Western blotting, ELISA or RIA assays employing EP1 specific antibodies.

Following expression of EP1 in a host cell, EP1 protein may be recovered to provide EP1 in active form, capable of binding EP1-specific ligands. Several EP1 purification procedures are available and suitable for use. Recombinant EP1 may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant EP1 can be separated from other cellular proteins by use of an immuno-affinity column made with monoclonal or polyclonal antibodies specific for full length nascent EP1, or polypeptide fragments of EP1.

Monospecific antibodies to EP1 are purified from mammalian antisera containing antibodies reactive against EP1 or are prepared as monoclonal antibodies reactive with EP1 using the technique of Kohler and Milstein, Nature 256: 495–497 (1975). Monospecific antibody as used herein is defined as a single antibody species or multiple antibody species with homogenous binding characteristics for EP1. Homogenous binding as used herein refers to the ability of the antibody species to bind to a specific antigen or epitope, such as those associated with the EP1, as described above. EP1 specific antibodies are raised by immunizing animals such as mice, rats, guinea pigs, rabbits, goats, horses and the like, with an appropriate concentration of EP1 either with or without an immune adjuvant.

Preimmune serum is collected prior to the first immunization. Each animal receives between about 0.1 µg and about 1000 µg of EP1 associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consisted of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of EP1 in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with EP1 are prepared by immunizing inbred mice, preferably Balb/c, with EP1. The mice are immunized by the IP or SC route with about 1 µg to about 100 µg, preferably about 10 µg, of $EP_1$ in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 µg of EP1 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using EP1 as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-EP1 mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of EP1 in body fluids or tissue and cell extracts.

It is readily apparent to those skilled in the art that the above described methods for producing monospecific antibodies may be utilized to produce antibodies specific for EP1 polypeptide fragments, or full-length EP1 polypeptide.

EP1 antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing EP1 or EP1 fragments are slowly passed through the column. The column is then washed with phosphate buffered saline until the optical density ($A_{280}$) falls to background, then the protein is eluted with 0.23 M glycine-HCl (pH 2.6). The purified EP1 protein is then dialyzed against phosphate buffered saline.

One method suitable for the isolation of DNA encoding the prostaglandin receptor of the present invention involves the utilization of amino acid and/or DNA sequence information obtained from other G-protein-linked receptors. Since other prostaglandin receptors are known to be G-protein linked, certain regions or domains such as the transmembrane and/or cytoplasmic domains, are expected to have some degree of homology sufficient to produce a probe for the isolation of novel receptors.

Prostaglandins and leukotrienes are known to transduce their signals via G-protein-linked receptors. Distinct receptors for $PGH_2$/thromboxane $A_2$, $PGI_2$, $PGE_2$, $PGD_2$, $PGF2\alpha$, $LTB_4$, and $LTD_4$ present in various tissues have been described. Some of the receptors have been solubilized and partially purified (Dutta-Roy, A. K. et al., (1987) JBC, 262, pp. 12685; Tsai, A. L. et al., (1989), JBC, 264, pp 61; 168-Watawabe, T. et. al., (1990), JBC, 265, pp. 21237) and the human platelet $TXA_2$ receptor has been purified to apparent homogeneity (Ushikubi, F. et. al., (1989), JBC, 264, pp. 16496). The purified thromboxane receptor exhibited a very broad band on a SDS-polyacrylamide gel centered at ≈57 kDa. Enough protein was obtained for partial sequence information.

Oligonucleotide probes were used to screen a human megakaryocytic cell line (MEG-01) cDNA library (Hirata, M. et al., (1991), Nature, 349, pp. 617). A partial length cDNA clone was obtained that, when sequenced, was found to encode the carboxy half of a putative G-protein linked receptor. This clone was then labeled and used to screen a human placenta library. One full-length (≈2.9 kb) clone contained extensive 5' and 3' noncoding regions and a 1029 bp open reading frame coding for a 343 amino-acid protein of $M_r$≈37000. The predicted sequence displays the characteristics of seven transmembrane G-linked receptors including two N-linked glycosylation sites (Asn-4 and Asn-16) in the putative extracellular amino terminal tail (29 residues), conserved Cys residues in extracellular loops 1 and 2 (Cys-105 and Cys-183), and several other conserved residues within transmembrane regions, with the exception of the Asp residue found in transmembrane 3, known to be essential for receptors with small amine-containing ligands (Strosberg, A. D., (1991), EJB, 196, pp 1). The sequence has a very short predicted third intracellular loop (27 residues). This portion of the molecule could possibly couple to the G-protein ($G_q$ or larger G-protein) responsible for interacting with phospholipase C and causing subsequent changes in calcium ion flux (Shenker, A. et al., (1991), JBC, 266, pp. 9309. 173-Moran, N. et al., (1990), Circulation, Suppl. 82, abstract 1830).

The coding region for the thromboxane receptor is extremely G+C-rich (70%). It was nearly impossible to isolate this cDNA from placenta or platelet reverse-transcribed RNA under normal conditions of denaturation (94–95° C.) with Taq polymerase. However, a shift of the denaturation temperature to 98° C. and use of Vent polymerase (New England Biolabs) enabled amplification of the complete cDNA.

The thromboxane receptor has been expressed in Xenopus oocytes. It can couple with endogenous signal transduction components to elicit a calcium-activated $Cl^-$ current recorded by electrophysiological measurement using the procedure described by Hirata, M. et al., (1991), Nature, 349, pp. 617. Binding studies have been performed with COS-1 cell membranes transfected by thromboxane receptor cDNA using the ligand S-145 (Hirata, M. et al., (1991), Nature, 349, pp. 617). We have also shown high affinity binding of the thromboxane antagonist SQ-29548 in human embryonic kidney 293 cells and membranes transfected with thromboxane-receptor cDNA with maximal binding of 2–3 pmol/mg protein. This level of expression is at least 5–10 times higher than in platelet membranes. On a per-cell basis assuming a 10% transfection efficiency, we estimate ≈$10^6$ binding sites/tranfected cell as compared to ≈1300 sites present on a platelet (Hourani, S. M. O. et al., (1991), Pharmacol. Rev., 43, pp. 243).

Northern-blot analysis revealed the presence of a 2.8-kb band in the MEG-01 cell line, placenta, and lung. The mRNA is probably in the low-abundance category, based on the reported long exposure time (12 days). and amount of $poly(A)^+$ RNA loaded (20 μg) to see detectable signals.

An approach to the isolation of other eicosanoid receptor genes by homology screening was taken, with the assumption that these receptors are related in primary structure (Sugimoto, Y. et al., (1992), JBC, 267, pp. 6463). Since these receptors are of the G-protein type there are areas of homology which are likely to be found in the transmembrane region and in the cytoplasmic domains. Therefore, various known G-protein linked receptors related to the prostaglandin receptors may be utilized to provide DNA probes to regions of the receptor protein-encoding DNA sought, which is likely to have homology, such as the transmembrane region.

Using a 0.3-kb thromboxane receptor cDNA fragment which encodes most of the transmembrane 5–7 region of this receptor, a 1.4-kb cDNA clone (EP1) hereinafter designated EP1 encoding a 402-amino acid receptor was isolated from a human erythroleukemia cell cDNA library. This protein, which was originally designated as an unknown "PGQ receptor", is now, hereafter, designated as the EP1 receptor and has two potential N-linked glycosylation sites (Asn-8 and Asn-25) and is extremely rich in basic (mainly arginine) and serine residues in the predicted third intracellular loop and the carboxy-terminal tail.

Like many other G-protein coupled receptors the EP1 receptor shares several common features. Firstly, there are 2 potential N-linked glycosylation sites (Asn8 and Asn25) in the putative extracellular amino terminus. Secondly, conserved cysteine residues are found in exofacial loops 1 and 2. The third cytoplasmic loop is relatively large (≈70 residues) and is extremely rich in basic amino acids (15 Arg, 3 His). In fact there is a heavy bias toward basic residues throughout the non-transmembrane segments of the protein. There are multiple serine residues, potential sites of protein kinase phosphorylation, throughout the C-terminus and third cytoplasmic loops. The EP1 receptor does not contain an aspartic acid residue in transmembrane three which is characteristic of the receptors binding cationic amino-containing ligands, however, it possesses a conserved arginine (position 338) found in all eicosanoid receptors within transmembrane seven. This region is the most highly conserved among the eicosanoid receptors. The EP1 receptor is most highly related to the human thromboxane receptor and the mouse EP3 receptors. It also shares some homology with the β3 adrenergic receptor which is of the same size (402 amino acids).

The novel prostaglandin receptor of the present invention is suitable for use in an assay procedure for the identification of compounds which modulate the receptor activity. Modulating receptor activity, as described herein includes the inhibition or activation of the receptor and also includes directly or indirectly affecting the normal regulation of the receptor activity. Compounds which modulate the receptor activity include agonists, antagonists and compounds which directly or indirectly affect regulation of the receptor activity.

The prostaglandin receptor of the present invention may be obtained from both native and recombinant sources for use in an assay procedure to identify receptor modulators. In general, an assay procedure to identify prostaglandin receptor modulators will contain the prostaglandin receptor of the present invention, and a test compound or sample which contains a putative prostaglandin receptor modulator. The test compounds or samples may be tested directly on, for example, purified receptor protein whether native or recombinant, subcellular fractions of receptor-producing cells whether native or recombinant, and/or whole cells expressing the receptor whether native or recombinant. The test compound or sample may be added to the receptor in the presence or absence of a known labelled or unlabelled receptor ligand. The modulating activity of the test compound or sample may be determined by, for example, analyzing the ability of the test compound or sample to bind to the receptor, activate the receptor, inhibit receptor activity, inhibit or enhance the binding of other compounds to the receptor, modifying receptor regulation, or modifying an intracellular activity.

The identification of modulators of EP1 receptor activity are useful in treating disease states involving the EP1 receptor activity. Other compounds may be useful for stimulating or inhibiting activity of the receptor. These compounds could be useful as antiinflammatory and antipyretic agents and analgesics. Such compounds could be of use in the treatment of diseases in which activation of the EP1 receptor results in either cellular proliferation, induction of cellular neoplastic transformations or metastatic tumor growth and hence could be used in the prevention and/or treatment of cancers such as colon cancer. The isolation and purification of an EP1-encoding DNA molecule would be useful for establishing the tissue distribution of EP1 receptors as well as establishing a process for identifying compounds which modulate EP1 receptor activity.

The following examples are provided for the purpose of illustrating the present invention without, however, limiting the same thereto.

EXAMPLE 1

Thromboxane Receptor cDNA Probe Preparation and Cloning of EP1 cDNA

A human thromboxane receptor cDNA fragment was isolated by PCR from reverse-transcribed placenta total RNA. 25 pmol of upstream primer 5'CTGTCCTTCCTGCTGAACACGGTCAGCGTG-3' (SEQ. ID. No.: 1) and downstream primer 5'-GCGGCGGAACAGGATATACACC-3' (SEQ. ID. No.: 2) were added together with 1 μg cDNA, dNTP (200 μM) and Vent polymerase (1 unit, New England Biolabs, Beverly, Mass.) in a 50 μl reaction volume (10 mM KCl/10 mM $(NH_4)_2SO_4$/20 mM Tris-HCl, (pH 8.8)/2 mM $MgSO_4$/0.1% (v/v) Triton X-100/100 μg/ml bovine serum albumin) for amplification at 98° C.-30 s; 62° C.-1 min; 72° C.-1 min for 40 cycles in a Perkin Elmer Cetus thermal cycler. The 312-bp product (nucleotides 628–939, Hirata et al., 1991, Supra) was isolated by agarose gel electrophoresis and Gene Clean purification (Bio101, La Jolla, Calif.).

A human erythroleukemia (HEL) cell cDNA library constructed in the lambda gt11 vector was screened with the $^{32}$P-labeled thromboxane receptor cDNA fragment under reduced stringency conditions (30% formamide/5×SSPE/5× Denhardt's solution/0.1% SDS/100 μg/ml sonicated salmon sperm DNA) at 42° C. overnight. Filters were washed briefly at room temperature with 2×SSC containing 0.1% SDS followed by washing (2×30 min) at 55° C. with 1×≈SSC containing 0.1% SDS. One positive phase clone (λ-TxR1) was plaque-purified and DNA was prepared by the plate lysate method (Sambrook et al., 1989 Molecular Cloning: A Laboratory Manual, 2 nd Ed., Cold Spring Harbor Laboratory, Cold Spring Harbor, N.Y.).

Subcloning and Sequencing of cDNA

Clone λ-TxR1 was digested with EcoRI and was found to contain three inserts of size 4.0 kb, 1.7 kb and 1.4 kb. Only the 1.4 kb insert was found to hybridize with the thromboxane receptor cDNA probe upon Southern blot analysis. The 1.4 kb EcoRI fragment (EP1) and various restriction fragments were subcloned into M13mp18 and M13mp19 vectors for sequencing at 70° C. with Taq polymerase (Gene ATAQ system, Pharmacia). The DNA was sequenced entirely on both strands at least two separate times using the M13 universal primer or primers generated from the determined sequence. The nucleotide sequence of EP1 is shown in Table 1. The amino acid sequence for the encoded protein is shown in Table 2. The 1.4 kb fragment (EP1; FIG. 1), when sequenced, was found to contain significant sequence homology to the human thromboxane receptor cDNA and the putative heptahelical arrangement characteristic of G protein-coupled receptors was evident. A long open reading frame (1206 bp) was determined which would result in 402 amino acid polypeptide with a predicted relative molecular mass of 41,858. The ATG assigned as the initiator codon matches the Kozak consensus sequence for translation initiation (Kozak, 1989 J. Cell. Biol., 108, pp 229–241). There are 74 bp of 5'untranslated sequence including an inframe TGA stop codon 60 bp upstream of the predicted start codon. Between these sequences one additional out-of-frame ATG is found with a 48 bp open reading frame terminating just after the predicted start. The EP1 cDNA contains a very short 3' untranslated region of about 112 base pairs which includes a polyadenylation signal, AATAAA, 19 bp upstream of a short poly(A) stretch of 19 residues.

EXAMPLE 2
Construction of Expression Vectors

The 1.4 kb EcoRI insert was subcloned into the EcoRI site of pcDNA1 (Invitrogen) and the correct orientation was verified by PstI digestion. In order to remove the 5' untranslated region with the upstream ATG, EP1 was cleaved with ApaI and the 1.25 kb ApaI fragment was purified. Kinased oligonucleotide 5'-CTAGCGGATCCCGCCATGAGCCCTTGCGGGCC-3' (SEQ. ID. No.: 5) and oligonucleotide 5'-CGCAAGGGCTCATGGCGGGATCCG-3' (SEQ. ID. No.: 6) were annealed and ligated to the ApaI fragment. Following ligation, the sample was subjected to cleavage with BamHI and the purified 1.3 kb band was ligated to BamHI-digested pcDNA1. The end-altered cDNA and orientation were verified by DNA sequencing.

TABLE 1

```
GGGGGCGGCAGGGCTGAGCGGCCGGTGATGGGGACCCCACATCCCAGGCAGTGCCGGCAC   (SEQ ID NO:3)
CCCTGGCGCCTGACATGAGCCCTTGCGGGCCCCTCAACCTGAGCCTGGCGGGCGAGGCGA
CCACATGCGCGGCGCCCTGGGTCCCCAACACGTCGGCCGTGCCGCCGTCGGGCGCTTCGC
CCGCGCTGCCCATCTTCTCCATGACGCTGGGCGCCGTGTCCAACCTGCTGGCGCTGGCGC
TGCTGGCGCAGGCCGCGGGCCGCCTGCGACGCCGCCGCTCGGCCACCACCTTCCTGCTGT
TCGTGGCCAGCCTGCTGGCCACCGACCTGGCGGGCCACGTGATCCCGGGCGCGCTGGTGC
TGCGTCTGTACACTGCGGGGCGCGCTCCGGCCGGCGGGGCCTGCCACTTCCTGGGCGGCT
GCATGGTCTTCTTCGGCCTGTGCCCGCTGCTGCTGGGCTGTGGCATGGCCGTGGAGCGCT
GCGTGGGCGTCACGCGGCCGCTGCTCCACGCCGCGCGGGTCTCGGTCGCCCGCGCGCGCC
TGGCGCTGGCCGCGGTGGCCGCGGTGGCCTTGGCCGTGGCGCTGCTGCCGCTGGCGCGCG
TGGGCCGCTATGAGCTGCAGTACCCGGGCACGTGGTGCTTCATCGGCCTGGGTCCCCCGG
GCGGCTGGCGCCAGGCACTGCTTGCTGGCCTCTTCGCCAGCCTCGGCCTGGTCGCGCTCC
TCGCCGCGCTGGTGTGCAACACGCTCAGCGGCCTGGCCCTGCATCGCGCCCGCTGGCGAC
GCCGCTCCCGACGGCCTCCCCCGGCCTCAGGCCCCGACAGCCGGCGTCGCTGGGGGGCGC
ACGGACCCCGCTCGGCCTCCGCCTCGTCCGCCTCGTCCATCGCTTCGGCCTCCACCTTCT
TTGGCGGCTCTCGGAGCAGCGGCTCGGCACGCAGAGCTCGCGCCCACGACGTGGAGATGG
TGGGCCAGCTTGTCGGTATCATGGTGGTGTCGTGCATCTGCTGGAGCCCAATGCTGGTGT
TGGTGGCGCTGGCCGTCGGCGGCTGGAGCTCTACCTCCCTGCAGCGGCCACTGTTCCTGG
CCGTGCGCCTTGCCTCCTGGAACCAGATCCTGGACCCTTGGGTGTACATCCTACTGCGCC
AGGCCGTGCTGCGCCAACTGCTTCGCCTCTTGCCCCCGAGGGCCGGAGCCAAGGGCGGCC
CCGCGGGGCTGGGCCTAACACCGAGCGCCTGGGAGGCCAGCTCGCTGCGCAGCTCCCGGC
ACAGCGGCCTCAGCCACTTCTAAGCACAACCAGAGGCCCAACGACTAAGCCAGCCCACCC
TGGGCTGGGCCCAGGTGCGCGGCGCAGAGCTTTGGGAATAAAAAGCCATTCTGCGAAAAA
AAAAAAAAAAAAAA
```

TABLE 2

```
MSPCGPLNLSLAGEATTCAAPWVPNTSAVPPSGASPALPIFSMTLGAVSNLLALALLAQA   (SEQ ID NO:4)
AGRLRRRRSATTFLLFVASLLATDLAGHVIPGALVLRLYTAGRAPAGGACHFLGGCMVFF
GLCPLLLGCGMAVERCVGVTRPLLHAARVSVARARLALAAVAAVALAVALLPLARVGRYE
LQYPGTWCFIGLGPPGGWRQALLAGLFASLGLVALLAALVCNTLSGLALHRARWRRRSRR
PPPASGPDSRRRWGAHGPRSASASSASSIASASTFFGGSRSSGSARRARAHDVEMVGQLV
GIMVVSCICWSPMLVLVALAVGGWSSTSLQRPLFLAVRLASWNQILDPWVYILLRQAVLR
QLLRLLPPRAGAKGGPAGLGLTPSAWEASSLRSSRHSGLSHF
```

EXAMPLE 3
Cloning of the EP1 cDNA into *E. coli* Expression Vectors

Recombinant EP1 is produced in *E. coli* following the transfer of the EP1 expression cassette into *E. coli* expression vectors, including but not limited to, the pET series (Novagen). The pET vectors place EP1 expression under control of the tightly regulated bacteriophage T7 promoter. Following transfer of this construct into an *E. coli* host which contains a chromosomal copy of the T7 RNA polymerase gene driven by the inducible lac promoter, expression of EP1 is induced when an appropriate lac substrate (IPTG) is added to the culture. The levels of expressed EP1 are determined by the assays described above.

The cDNA encoding the entire open reading frame for EP1 is inserted into the NdeI site of pET 11a. Constructs in the positive orientation are identified by sequence analysis and used to transform the expression host strain BL21. Transformants are then used to inoculate cultures for the production of EP1 protein. Cultures may be grown in M9 or ZB media, whose formulation is known to those skilled in the art. After growth to an approximate $OD_{600}=1.5$, expression of $EP_1$ is induced with 1 mM IPTG for 3 hours at 37° C. Authentic EP1 enzymatic activity may be found in the insoluble inclusion body fraction from these cells. Soluble EP1 is extracted from the inclusion body fraction with 5 M guanidine-HCl in a buffer containing 50 mM Tris-HCl (pH 8) and 100 mM dithiothreitol. Active EP1 is generated from this extract following dialysis against 100 volumes of 25 mM HEPES (pH 7.5), 5 mM dithiothreitol, 10% sucrose.

EXAMPLE 4
In Vitro Translation of EP1 mRNA by Xenopus Oocyte Microinjection Vector and Expression in Mammalian Cells EP1 cDNA constructs are ligated into in vitro transcription vectors (the pGEM series, Promega) for the production of synthetic mRNAs.

Synthetic mRNA is produced in sufficient quantity in vitro by cloning double stranded DNA encoding EP1 mRNA into a plasmid vector containing a bacteriophage promoter, linearizing the plasmid vector containing the cloned EP1-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded EP1-encoding DNA is cloned into the bacteriophage promoter containing vector in the proper orientation using one or more of the available restriction endonuclease cloning sites on the vector which are convenient and appropriate for cloning EP1 DNA. The vector with the ligated EP1 DNA is used to transform bacteria, and clonal isolates are analyzed for the presence of the vector with the EP1 DNA in the proper orientation.

Once a vector containing the EP1-encoding DNA in the proper orientation is identified and isolated, it is linearized by cleavage with a restriction endonuclease at a site downstream from, and without disrupting, the EP1 transcription unit. The linearized plasmid is isolated and purified, and used as a template for in vitro transcription of EP1 mRNA.

The template DNA is then mixed with bacteriophage-specific DNA-dependent RNA polymerase in a reaction mixture which allows transcription of the DNA template forming EP1 mRNA. Several bacteriophage-specific DNA-dependent RNA polymerases are available, including but not limited to T3, T7, and SP6 RNA polymerase. The synthetic EP1 mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5'terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified EP1 mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic EP1 mRNA to produce EP1 protein. The microinjected oocytes are incubated to allow translation of the EP1 mRNA, forming EP1 protein.

These synthetic mRNAs are injected into Xenopus oocytes (stage 5-6) by standard procedures [Gurdon, J. B. and Wickens, M. D. Methods in Enzymol. 101: 370–386, (1983)]. Oocytes are harvested and analyzed for EP1 expression as described below.

EXAMPLE 5
pcDNA-EP1 Expression in Xenopus Oocytes

Oocytes were taken from adult females of *Xenopus laevis* using standard surgical procedure (Colman, A., 1984 In: Transcription and Translation—A Practical Approach, IRL Press). To remove follicle cells, oocytes were treated for 2–3 h with freshly made collagenase (2 mg/ml, type 2, Worthington Biochemical Corp., Freehold, N.J.) in $Ca^{2+}$-free ND96 solution (ND96 in mM: NaCl 96, KCl 2, $MgCl_2$ 1, HEPES 5, Na-pyruvate 2.5, theophylline 0.5, gentamicin 50 mg/ml, +1.8 $CaCl_2$, pH 7.6). Defolliculated stage 5-6 oocyte were selected and maintained in ND96 solution. Ooctye nuclei were injected with 1–5 ng of pcDNA-EP1 or pcDNA-EP1 (Bam) and then incubated at 18° C. for 48 h before challenge with agonist. Functional activity was determined by measurement of either agonist-induced $Ca^{2+}$-dependent $Cl^-$ current or light emission in oocytes injected with the $Ca^{2+}$-specific photoprotein aequorin (J. Blinks, Friday Harbor Photoproteins, Washington), (Giladi and Spindel 1991 Biotechniques, 10, pp 744–747). For the electrophysiological assays an ooctye was placed in a 0.5 ml perfusion chamber and voltage clamped at −60 mV (with microelectrodes of 0.5–2.0 MΩ resistance filled with 3 M KCl) using a Turbo TEC 01C amplifier (NP1 Instruments, Germany). Ligand-containing solution was perfused and the current response was recorded. For the luminometric assay, aequorin-loaded oocytes (100 ng/ooctye) were placed individually in cuvettes containing 0.4 ml ND96 and the light emission provoked by ligand addition was recorded using a Bio-Orbit 1251 luminometer (Fisher Sci. Ltd.).

Figure 4A:
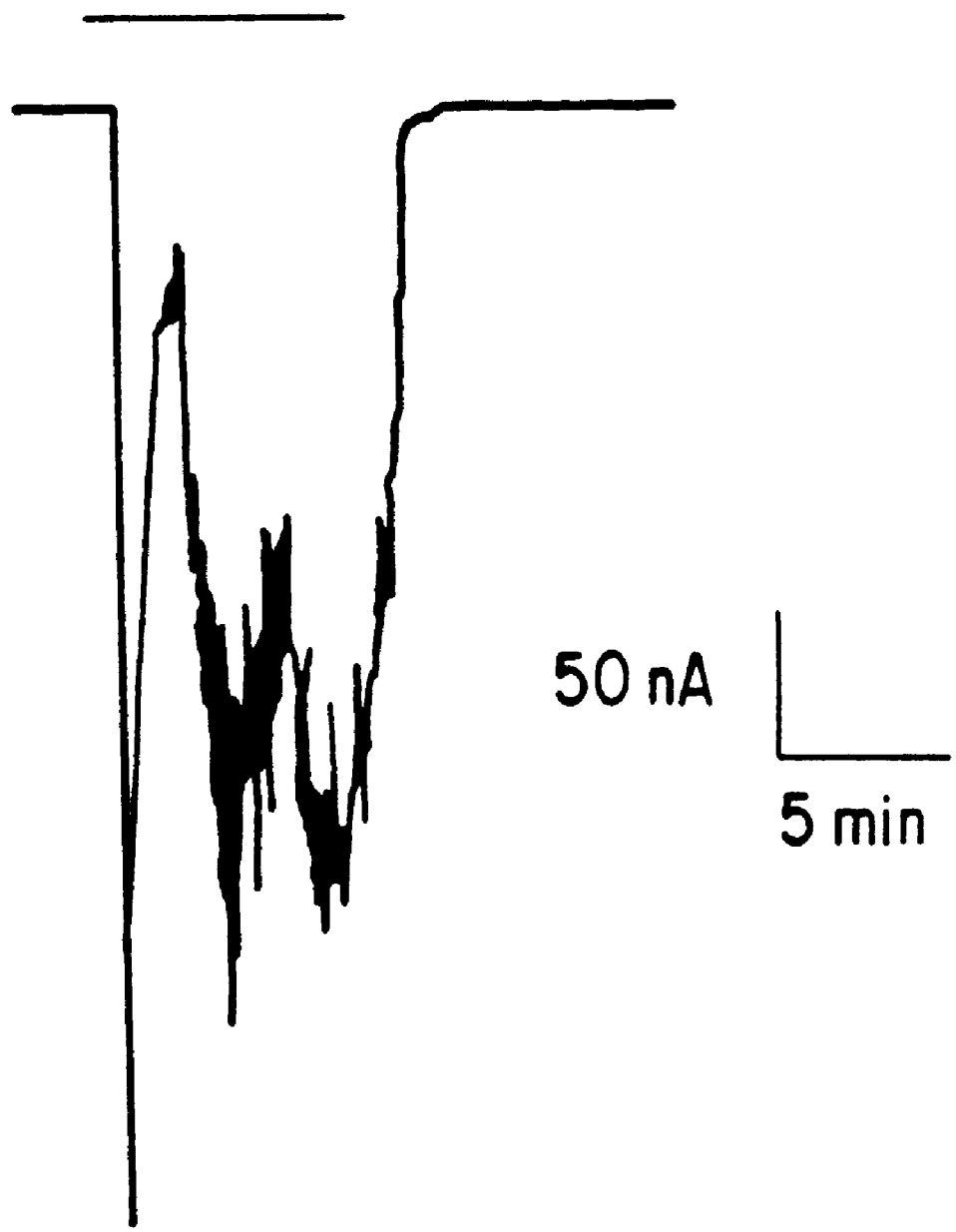
FIG. 4A–E—Expression of prostaglandin $E_2$ receptor in Xenopus oocytes. Panel A: An inward $Ca^2$—dependent $Cl^-$ current (shown as downward deflection) evoked by bath perfusion of 1 $\mu$M $PGE_2$. The oocyte was injected with 5 ng of pcDNA-EP1 (Bam) and voltage-clamped at −60 mV. Panel B–D: $PGE_2$-induced light responses in aequorin loaded oocytes. The intensity of aequorin light emission is expressed in relative units and the background emission typically was 0.5–0.7 units units. The $PGE_2$ was injected into the recording cuvette at 10 s at a final concentration indicated on each trace Panel E; Light responses were evoked by different concentrations of $PGE_2$ and $PGF_{2\alpha}$. Each bar represents the mean±s.e.m. of data from 10 to 15 oocytes from 4 donors. Data are expressed as the percentage of the response observed with 1 $\mu$M of $PGE_2$.
Figure 4B:
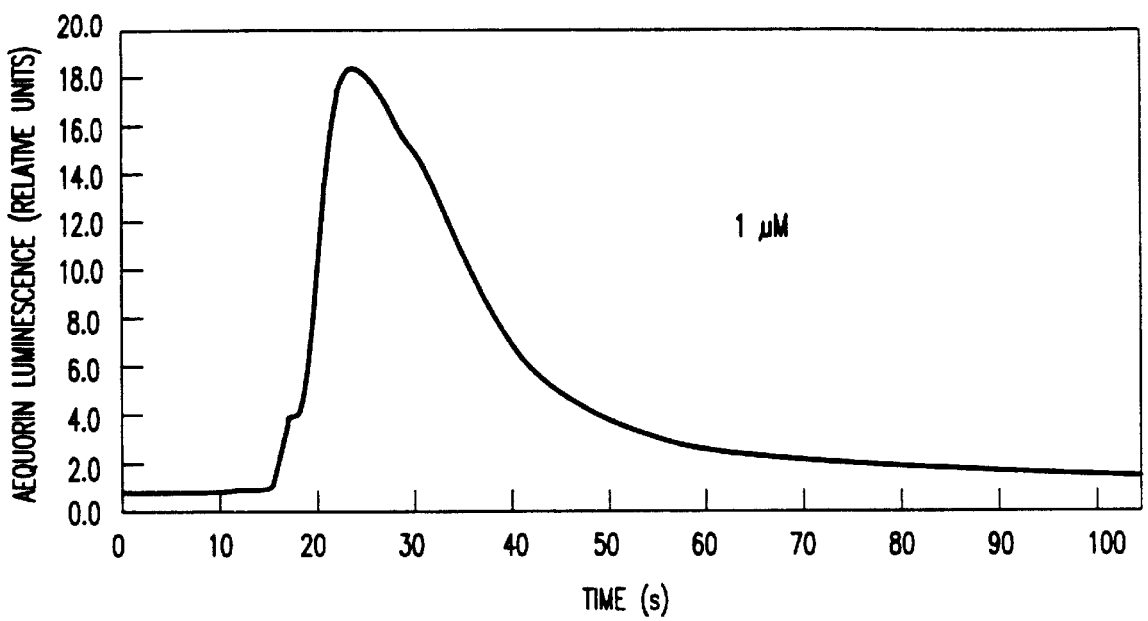
Figure 4C:
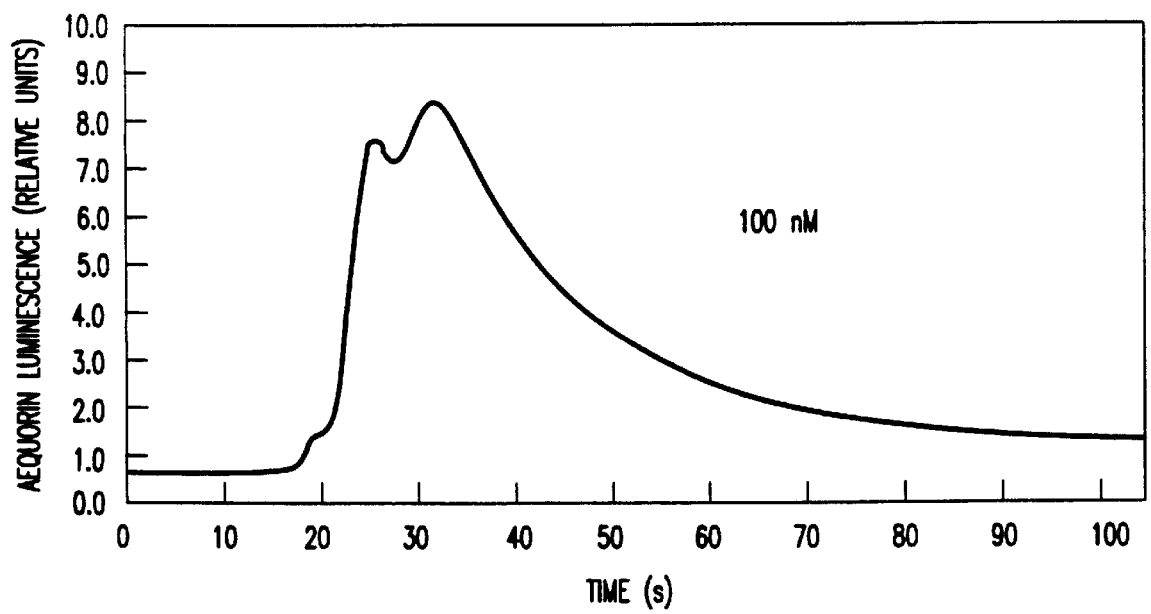
Figure 4D:
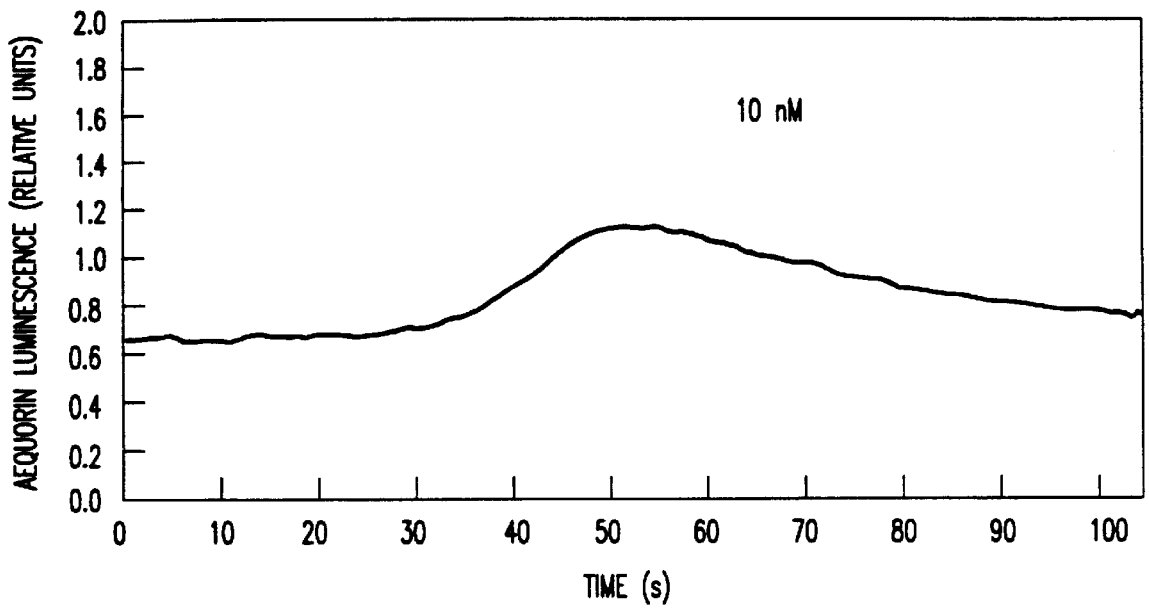
Figure 4E:
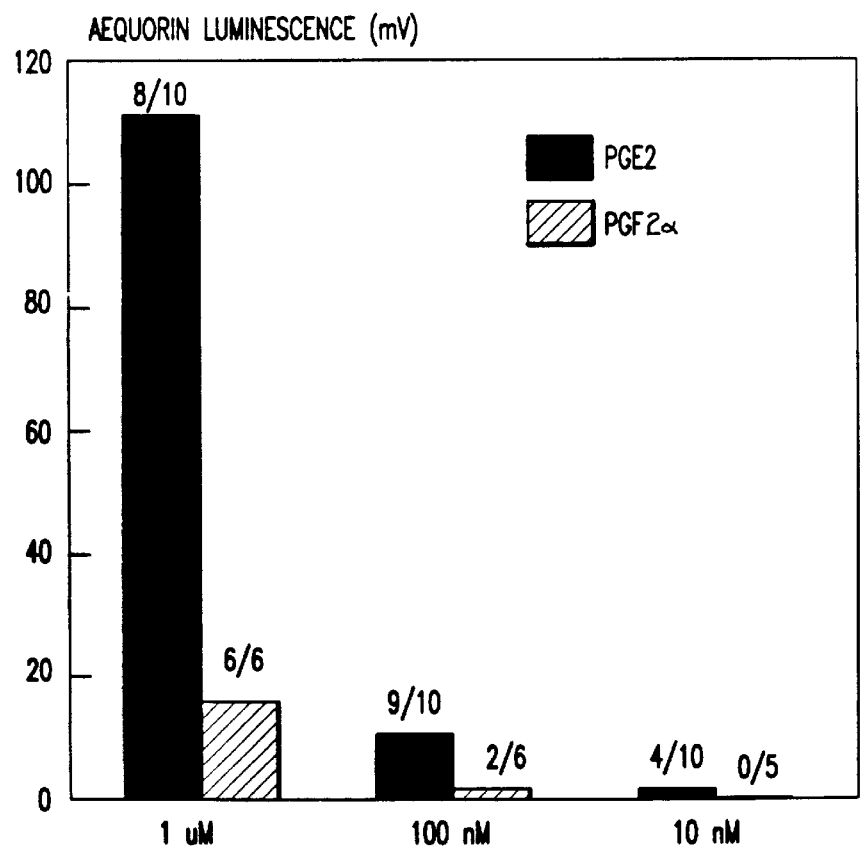

Functional activity was determined in pcDNA-EP1-injected oocytes using electrophysiological and aequorin luminescence assays. In the electrophysiological assay, perfusion of 1 μM to 10 mM $PGE_2$ resulted in prominent current responses in oocytes injected with pcDNA-EP1 suggesting that this clone encodes a functional EP1 receptor that is coupled to the phosphatidylinositol/$Ca^{2+}$ signalling pathway, FIG. 4A. Such responses were absent in control $H_2O$-injected) oocytes. Ligand induced increases in intracellular $Ca^{2+}$ were also demonstrated directly by light emission in aequorin-loaded oocytes, FIGS. 4B–D. The dose-response dependencies obtained from aequorin luminescence assay indicated that $PGE_2$ was more potent agonist of the expressed receptor when compared to $PGF_{2\alpha}$, FIG. 4E.

EXAMPLE 6

Cloning of EP1 cDNA into a Mammalian Expression Vector

EP1 cDNA expression cassettes are ligated at appropriate restriction endonuclease sites to the following-vectors containing strong, universal mammalian promoters: pBC12BI [Cullen, B. R. Methods in Enzymol. 152: 684–704 1988], and pEE12 (CellTech EPO 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978–120 and 139778–121 using pD5 (Berker and Sharp, Nucl. Acid Res. 13: 841–857 [1985]) as template. The resulting 0.25 Kb PCR product is digested with ClaI and SpeI and ligated into the 6.7 Kb fragment of pEE12 which had been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the EP1 cDNA in the positive orientation with respect to the promoter are ligated into appropriate restriction sites 3' of the promoter and identified by restriction site mapping and/or sequencing. These cDNA expression vectors are introduced into various host cells including, but not limited to: [COS-7 (ATCC# CRL1651), CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture extracts can be harvested and analyzed for EP1 expression as described below.

All of the vectors used for mammalian transient expression can be used to establish stable cell lines expressing EP1. Unaltered EP1 cDNA constructs cloned into expression vectors will be expected to program host cells to make intracellular EP1 protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing EP1 cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz. L. and Davies, J., GENE 25: 179 (1983)]; APRT, xanthine-guanine phosphoribosyl-transferase, pMAM (Clontech) [Murray, et al., Gene 31: 233 (1984)] will allow for the selection of stably transfected clones. Levels of EP1 are quantitated by the assays described above.

EP1 cDNA constructs are ligated into vectors containing amplifiable drug-resistance markers for the production of mammalian cell clones synthesizing the highest possible levels of EP1. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR-CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thyymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 7 pcDNA-EP1 Expression in COS-M6 Cells and [$^3$H]PGE$_2$ Binding Assays

The pcDNA-EP1 plasmid was transfected into COS-M6 Cells using the DEAE-dextran method. The cells were maintained in culture for 72 h, then harvested and membranes prepared by differential centrifugation (1000×g or 10 min, then 100,000×g for 30 min) following lysis of the cells by nitrogen cavitation (Frey, et al., 1993). [3H]Prostaglandin E2 ([$^3$H]PGE$_2$) binding assays were performed in 10 mM potassium phosphate (pH 6.0), containing 1 mM EDTA, 0.5 nM [$^3$H]PGE$_2$ (154 Ci/mmol; DuPont-New England Nuclear) and 60–100 µg of protein from the 100,000×g membrane fraction. Incubations were conducted for 1 h at room temperature prior to separation of the bound and free radioligand by rapid filtration as previously described (Frey et al., 1993 Eur. J. Mol. Pharmacol., 244, pp 239–250). Residual [3H]PGE$_2$ bound to the filter was quantitated by liquid scintillation counting. Specific binding was defined as the difference between total binding and non-specific binding, determined in the presence of 1 µM PGE$_2$.

Figure 3B:
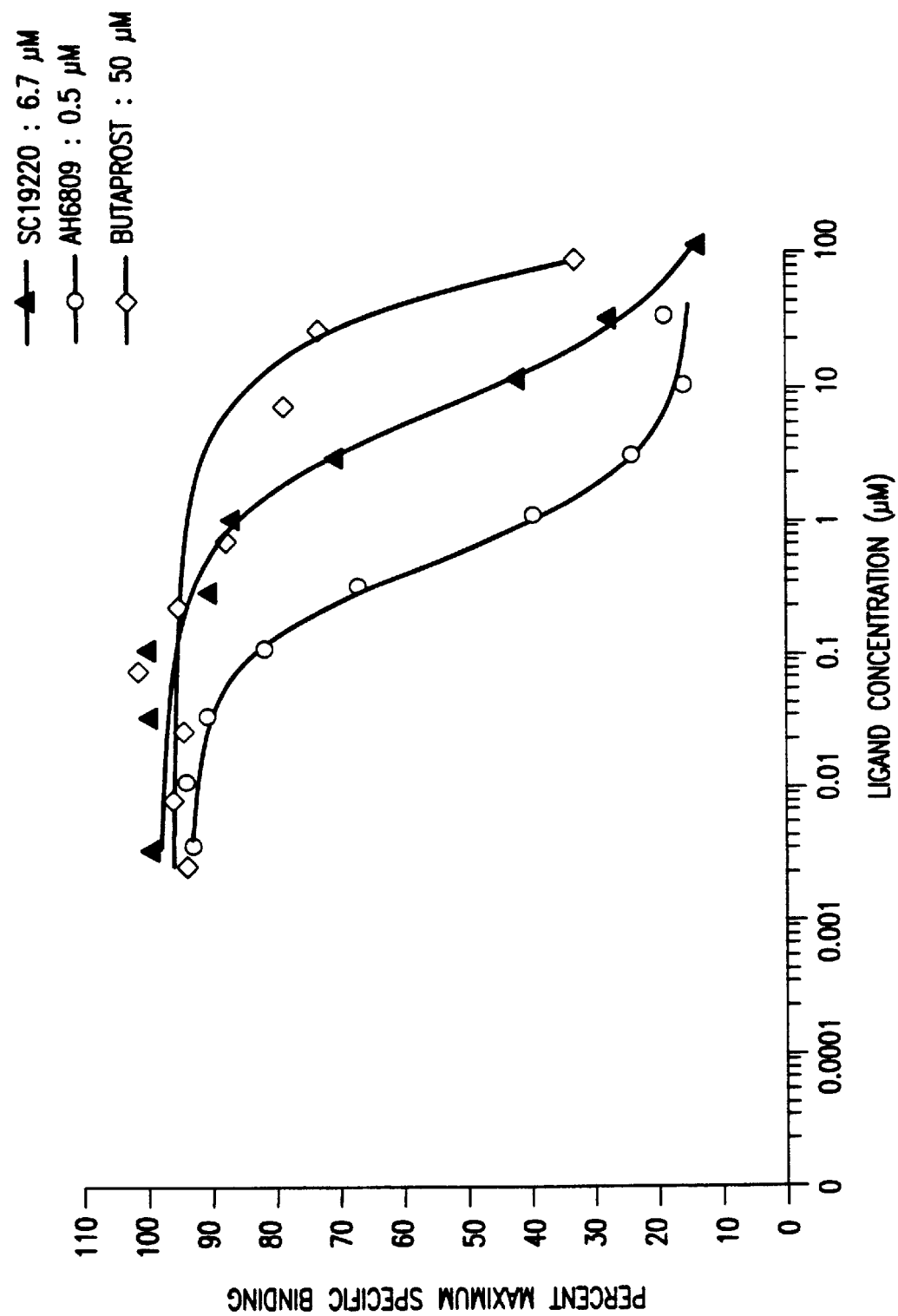

The data showing a dose-dependent increase in intracellular calcium in pcDNA-EP1 injected oocytes challenged with PGE$_2$, suggested that this receptor was the prostaglandin E receptor EP1 subtyped. In order to confirm this, [$^3$H]PGE$_2$ binding assays were performed with membranes prepared from pcDNA-EP1 and pcDNA-EP1(Bam) transfected COS-M6 cells. [$^3$H]PGE$_2$ bound specifically to these cell membranes, but not to membranes prepared from COS M6 cells transfected with pcDNA alone. Scatchard analysis showed the [$^3$H]PGE$_2$ specific binding to pcDNA-EP1 transfected COS-M6 cell membranes was of high affinity and saturable, with an equilibrium dissociation constant (K$_D$) of 1 nM and with the maximum number of specific binding sites (B$_{max}$) being approximately 360 fmol/mg of protein. In addition, prostaglandins competed for [$^3$H]PGE$_2$ specific binding with the rank order of potency expected for competition at the EP$_1$ subtype with PGE$_2$>PGE$_1$>PGF$_{2\alpha}$>>PGD$_2$, FIG. 3A. Moreover the selective-EP$_1$ antagonists AH 6809 and SC 19220 competed for [$^3$H]PGE$_2$ specific binding with IC50 values of approximately 0.5 μM and 6.7 μM, in agreement with the potencies for these compouned determined in smooth muscle contraction assays (Coleman et al., 1985 Br. J. Pharmacol, 85, pp. 286P). Finally, the potent EP$_2$ agonist butaprost was relatively inactive at the specific binding sites with an IC50 value of 50 μM, FIG. 3B. These radioligand binding data demonstrate that the EP$_1$ receptor has the characteristics of the EP$_1$ subtyped.

EXAMPLE 8

Cloning of EP$_1$ cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing EP$_1$ cDNA is produced by the following standard methods (InVitrogen Maxbac Manual): the EP1 cDNA constructs are ligated downstream of the polyhedrin promoter in a variety of baculovirus transfer vectors, including the pAC360 and the pBlueBac vector (In Vitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of β-galactosidase expression (Vialard, et al. 1990, J. Virol., 64, pp 37–50). Following plaque purification and infection of sf9 cells with EP1 recombinant baculovirus, EP1 expression is measured by the assays described above.

The cDNA encoding the entire open reading frame for EP1 is inserted into the BamHI site of pBlueBacII. Constructs in the positive orientation with respect to the polyhedrin promoter are identified by sequence analysis and used to transfect Sf9 cells in the presence of linear AcNPV mild type DNA.

Authentic, active EP1 is found associated with the membranes of infected cells. Membrane preparations are prepared from infected cells by standard procedures.

EXAMPLE 9

Cloning of EP1 cDNA into a Yeast Expression Vector

Recombinant EP1 is produced in the yeast *S. cerevisiae* following the insertion of the optimal EP1 cDNA construct into expression vectors designed to direct the intracellular expression of heterologous proteins. For intracellular expression, vectors such as EmBLyex4 or the like are ligated to the EP1 cistron [Rinas, U. et al., Biotechnology 8: 543–545 (1990); Horowitz B. et al., J. Biol. Chem. 265: 4189–4192 (1989)]. The levels of expressed EP1 are determined by the assays described above.

EXAMPLE 10

Purification of Recombinant EP$_1$

Recombinantly produced EP$_1$ may be purified by antibody affinity chromatography.

EP1 antibody affinity columns are made by adding the anti-EP1 antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized EP1 or EP1 subunits are slowly passed through the column. The column is then washed with phosphate-buffered saline together with detergents until the optical density (A280) falls to background, then the protein is eluted with 0.23 M glycine-HCl (pH 2.6) together with detergents. The purified EP1 protein is then dialyzed against phosphate buffered saline.

What is claimed is:

1. A method of determining whether a test compound modulates a signal transduction activity of a prostaglandin receptor $EP_1$, comprising:
   a) culturing $EP_1$-receptor-expressing host cells under conditions that would allow expression of a recombinant prostaglandin receptor, said host cells being transfected with a nucleic acid molecule encoding said recombinant prostaglandin $EP_1$-receptor comprising the amino acid sequence as set forth in SEQ ID NO:4:
   b) exposing the $EP_1$ receptor-expressing host cells of step a) to the test compound;
   c) exposing control host cells to the test compound of step b), wherein said control host cells do not express recombinant prostaglandin $EP_1$ receptor protein;
   d) measuring the modulating affect of the test compound which interacts with the recombinant $EP_1$ receptor from the host cells of step a) and control host cells of step c); and,
   e) comparing the modulating affect of the test compound on the host cells and control host cells.

2. The method of claim 1 wherein said host cells are Xenopus oocytes.

3. The method of claim 1 wherein the effect is measured by an electrophysiological assay.

4. The method of claim 3 wherein said host cells are Xenopus oocytes.

5. The method of claim 4 wherein the nucleic acid molecule is mRNA.

6. The method of claim 1 wherein the nucleic acid molecule is DNA, wherein said $EP_1$ receptor-expressing host cells are transiently or stably transformed by said DNA molecule.

7. A method of determining whether a test compound modulates a signal transduction activity of a prostaglandin receptor $EP_1$, comprising:
   a) culturing $EP_1$-receptor-expressing host cells under conditions that would allow expression of a recombinant prostaglandin receptor, said host cells being transfected with a nucleic acid molecule encoding said recombinant prostaglandin $EP_1$-receptor comprising the amino acid sequence as set forth in SEQ ID NO:4;
   b) exposing a first population of $EP_1$ receptor-expressing cells of step a) to a known prostaglandin $EP_1$ receptor ligand;
   c) exposing a second population of $EP_1$ receptor-expressing cells of step a) to the test compound and the known prostaglandin $EP_1$-receptor ligand of step b);
   d) exposing control host cells to the test compound of step c), wherein said control host cells do not express recombinant prostaglandin $EP_1$ receptor protein;
   e) measuring the modulating affect of the test compound, which interacts with recombinant $EP_1$ protein, in the presence and absence of the known $EP_1$ receptor ligand, from the cells of step b), step c) and step d); and,
   f) comparing the modulating affect of the test compound as determined from step b), step c) and step d.

8. The method of claim 7 wherein said host cells are Xenopus oocytes.

9. The method of claim 7 wherein the effect is measured by an electrophysiological assay.

10. The method of claim 7 wherein said known prostaglandin $EP_1$ receptor ligand is a ligand which shows 50% maximum specific binding to the prostaglandin $EP_1$ receptor protein at a concentration of up to 0.05 µM when competing with labeled $PGE_2$ for binding to the prostaglandin $EP_1$ receptor protein.

11. The method of claim 9 wherein said known, labeled prostaglandin $EP_1$ receptor ligand is selected from the group consisting of $PGE_2$, $PGE_1$, $PGF_{2\alpha}$ and AH6809.

12. The method of claim 9 wherein said host cells are Xenopus oocytes.

13. The method of claim 12 wherein the nucleic acid molecule is mRNA.

14. The method of claim 7 wherein the nucleic acid molecule is DNA, wherein said $EP_1$ receptor-expressing host cells are transiently or stably transformed by said DNA molecule.

15. A method of determining whether a test compound competes with a known prostaglandin $EP_1$ receptor ligand for binding to a prostaglandin $EP_1$ receptor protein, comprising:
   a) culturing $EP_1$-receptor-expressing host cells under conditions that would allow expression of a recombinant prostaglandin receptor, said host cells being transfected with a nucleic acid molecule encoding said recombinant prostaglandin $EP_1$-receptor comprising the amino acid sequence as set forth in SEQ ID NO:4;
   b) isolating a substantially purified cell membrane preparation from the $EP_1$ receptor-expressing cells of step a);
   c) exposing a first population of the purified cell membrane preparation of step b) to a known, labeled prostaglandin $EP_1$ receptor ligand;
   d) exposing a second population of the purified cell membrane preparation of step b) to the test compound and the known, labeled prostaglandin $EP_1$ receptor ligand;
   e) determining the binding of the known, labeled prostaglandin $EP_1$ receptor ligand to the membrane preparations of step c) and step d); and,
   f) comparing the binding of the known, labeled prostaglandin $EP_1$ receptor ligand protein to the membrane preparations:of step c) and step d).

16. The method of claim 15 wherein said known prostaglandin $EP_1$ receptor ligand is a ligand which shows 50% maximum specific binding to the prostaglandin $EP_1$ receptor protein at a concentration of up to 0.05 µM when competing with labeled $PGE_2$ for binding to the prostaglandin $EP_1$ receptor protein.

17. The method of claim 15 wherein said known, labeled prostaglandin $EP_1$ receptor ligand is selected from the group consisting of $PGE_2$, $PGE_1$, $PGF_{2\alpha}$ and AH6809.

18. The method of claim 15 wherein the nucleic acid molecule is DNA, wherein said $EP_1$ receptor-expressing host cells are transiently or stably transformed by said DNA molecule.

19. A method of determining whether a test compound competes with a known prostaglandin $EP_1$ receptor ligand for binding to a prostaglandin $EP_1$ receptor protein, comprising:
   a) culturing $EP_1$-receptor-expressing host cells under conditions that would allow expression of a recombinant prostaglandin receptor, said host cells being transfected with a nucleic acid molecule encoding said recombinant prostaglandin $EP_1$-receptor comprising the amino acid sequence as set forth in SEQ ID NO:4;
   b) lysing the $EP_1$ receptor expressing host cells of step a);
   c) exposing a first population of the lysed cells of step b) to a known, labeled prostaglandin $EP_1$ receptor ligand;
   d) exposing a second population of the lysed cells of step b) to the test compound and the known, labeled prostaglandin $EP_1$ receptor ligand;
   e) determining the binding of the known, labeled prostaglandin $EP_1$ receptor ligand to the $EP_1$ receptor from the lysed cells of step c) and step d); and,
   f) comparing the binding of the known, labeled prostaglandin $EP_1$ receptor ligand protein to the $EP_1$ receptor from the lysed cells of step c) and step d).

20. The method of claim 19 wherein said known prostaglandin $EP_1$ receptor ligand is a ligand which shows 50% maximum specific binding to the prostaglandin $EP_1$ receptor protein at a concentration of up to 0.05 µM when competing with labeled $PGE_2$ for binding to the prostaglandin $EP_1$ receptor protein.

21. The method of claim 19 wherein said known, labeled prostaglandin $EP_1$ receptor ligand is selected from the group consisting of $PGE_2$, $PGE_1$, $PGF_{2\alpha}$ and AH6809.

22. The method of claim 19 wherein the nucleic acid molecule is DNA, wherein said $EP_1$ receptor-expressing host cells are transiently or stably transformed by said DNA molecule.

23. A method of determining whether a test compound competes with a known prostaglandin $EP_1$ receptor ligand for binding to a prostaglandin $EP_1$ receptor protein, comprising:
   a) culturing $EP_1$-receptor-expressing host cells under conditions that would allow expression of a recombinant prostaglandin receptor, said host cells being transfected with a nucleic acid molecule encoding said recombinant prostaglandin $EP_1$-receptor comprising the amino acid sequence as set forth in SEQ ID NO:4;
   b) exposing a first population of $EP_1$ receptor-expressing cells of step a) to a known, labeled prostaglandin $EP_1$ receptor ligand;
   c) exposing a second population of $EP_1$ receptor-expressing cells of step a) to the compound and the known, labeled prostaglandin $EP_1$-receptor ligand of step b);
   d) determining the binding of the known, labeled prostaglandin $EP_1$ receptor ligand to the membrane preparations of step b) and step c); and,
   e) comparing the binding of the known, labeled prostaglandin $EP_1$ receptor ligand protein to the membrane preparations of step b) and step c).

24. The method of claim 23 wherein said known prostaglandin $EP_1$ receptor ligand is a ligand which shows 50% maximum specific binding to the prostaglandin $EP_1$ receptor protein at a concentration of up to 0.05 µM when competing with labeled $PGE_2$ for binding to the prostaglandin $EP_1$ receptor protein.

25. The method of claim 23 wherein said known, labeled prostaglandin $EP_1$ receptor ligand is selected from the group consisting of $PGE_2$, $PGE_1$, $PGF_{2\alpha}$ and AH6809.

26. The method of claim 23 wherein the nucleic acid molecule is DNA, wherein said $EP_1$ receptor-expressing host cells are transiently or stably transformed by said DNA molecule.

* * * * *